(12) United States Patent
House et al.

(10) Patent No.: US 6,652,814 B1
(45) Date of Patent: Nov. 25, 2003

(54) STRIP HOLDER FOR USE IN A TEST STRIP METER

(75) Inventors: Allen House, Danville, CA (US); Lorin Olson, Scotts Valley, CA (US)

(73) Assignee: LifeScan, Inc., Milpitas, CA (US)

( * ) Notice: Subject to any disclaimer, the term of this patent is extended or adjusted under 35 U.S.C. 154(b) by 209 days.

(21) Appl. No.: 09/637,466

(22) Filed: Aug. 11, 2000

(51) Int. Cl.[7] .................................................. B01L 9/00
(52) U.S. Cl. ........................... 422/104; 422/55; 422/56; 422/61; 422/82.05; 422/99; 422/103; 422/104; 436/164; 436/174
(58) Field of Search ............................... 422/55, 56, 58, 422/61, 68.1, 82.05, 99, 103, 104; 436/43, 46, 48, 164, 165, 169, 172, 174, 178

(56) References Cited

U.S. PATENT DOCUMENTS

| | | | | |
|---|---|---|---|---|
| 3,620,676 A | | 11/1971 | Davis ........................... 23/253 |
| 3,640,267 A | | 2/1972 | Hurtrg et al. ................... 128/2 |
| 4,088,448 A | | 5/1978 | Lilja et al. ..................... 23/259 |
| 4,426,451 A | | 1/1984 | Columbus ..................... 436/518 |
| 4,797,256 A | * | 1/1989 | Watlington, IV ............. 422/58 |
| 4,868,129 A | | 9/1989 | Gibbons et al. ............. 436/179 |
| 4,934,817 A | * | 6/1990 | Gassenhuber ................ 356/446 |
| 5,104,813 A | | 4/1992 | Besemer et al. ............. 436/179 |
| 5,208,163 A | | 5/1993 | Charlton et al. ............... 436/63 |
| 5,230,866 A | | 7/1993 | Shartle et al. ................ 422/103 |
| 5,281,395 A | * | 1/1994 | Markhart et al. ......... 422/82.05 |
| 5,424,035 A | * | 6/1995 | Hones et al. ................. 422/55 |
| 5,597,532 A | * | 1/1997 | Connolly ...................... 422/58 |
| 5,700,695 A | | 12/1997 | Yassinzadeh et al. ....... 436/180 |
| 5,714,123 A | * | 2/1998 | Sohrab ......................... 422/99 |
| 5,736,404 A | | 4/1998 | Yassinzadeh et al. ......... 436/52 |
| 5,780,304 A | | 7/1998 | Matzinger et al. |
| 5,795,543 A | * | 8/1998 | Poto et al. ................ 422/82.05 |
| 5,872,713 A | | 2/1999 | Douglas et al. |
| 6,106,780 A | * | 8/2000 | Douglas et al. ............... 422/58 |
| 6,180,063 B1 | * | 1/2001 | Markhart .................. 422/82.05 |
| 6,315,738 B1 | * | 11/2001 | Nishikawa et al. .......... 600/583 |
| 6,335,203 B1 | * | 1/2002 | Patel et al. .................. 436/169 |
| 6,458,326 B1 | * | 10/2002 | Modzelewski et al. .... 422/68.1 |

FOREIGN PATENT DOCUMENTS

| | | |
|---|---|---|
| EP | 0394048 | 10/1990 |
| EP | 0502691 | 9/1992 |
| EP | 803288 | 10/1997 |

* cited by examiner

*Primary Examiner*—Jill Warden
*Assistant Examiner*—Dwayne K Handy
(74) *Attorney, Agent, or Firm*—Susan C. Tall; Carol M. LaSalle; Bozicevic, Field & Francis, LLP

(57) ABSTRACT

Test strip holders for use with test strip meters are provided. The subject test strip holders include at least an opening and a lip associated with the opening. The lip element of the subject holders is capable of forming a liquid seal with the upper surface of a test strip upon insertion of the test strip into the opening. In many embodiments, the strip holder is configured to at least partially encompass a sample application region of a test strip upon insertion of the strip into the opening. Also provided are meters on which the subject test holders are present, as well as methods for using the same.

7 Claims, 7 Drawing Sheets

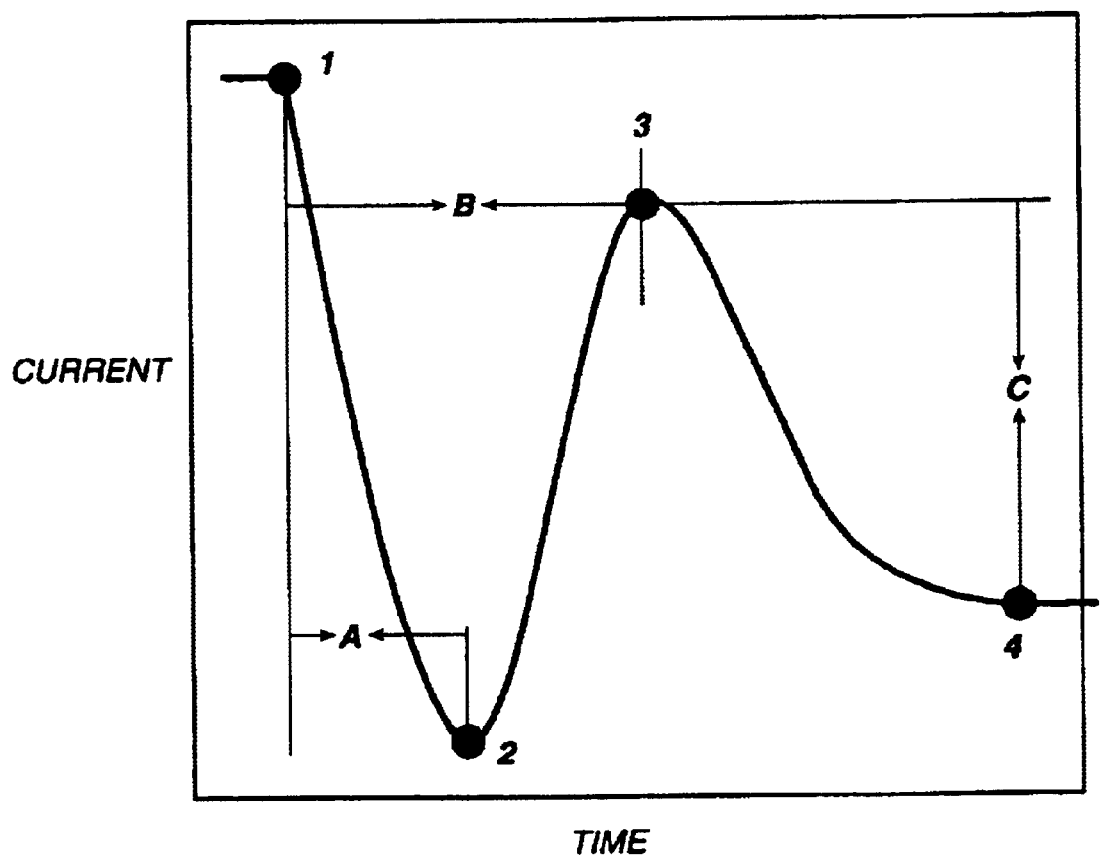

STRIP HOLDER FOR USE IN A TEST STRIP METER

FIELD OF THE INVENTION

The field of this invention is fluidic medical diagnostic devices for measuring the concentration of an analyte in or a property of a biological fluid.

BACKGROUND OF THE INVENTION

A variety of medical diagnostic procedures involve tests on biological fluids, such as blood, urine, or saliva, and are based on a change in a physical characteristic of such a fluid or an element of the fluid, such as blood serum. The characteristic can be an electrical, magnetic, fluidic, or optical property. When an optical property is monitored, these procedures may make use of a transparent or translucent device to contain the biological fluid and a reagent. A change in light absorption of the fluid can be related to an analyte concentration in, or property of, the fluid.

A growing number of assay formats employ a disposable test strip, fluidic device or card which is used in conjunction with a meter. The disposable fluid device receives the sample to be assayed and includes any reagents necessary for the assay to be conducted. The test strip also typically includes one or more flow paths through which the sample flows during the assay.

As mentioned above, these test strips are typically used in conjunction with a meter which is capable of receiving a signal originated in a measurement area of the card. To receive the signal from the measurement area, the test strip is generally inserted into an opening in the meter so that at least the measurement area of the test strip is present inside the meter. Examples of assay systems that are made up of these types of disposable test strips and meters may be found in application Ser. No. 09/333765, filed Jun. 15, 1999; and Ser. No. 09/356248, filed Jul. 16, 1999; the disclosures of which are herein incorporated by reference.

Because the test strip is inserted into the meter in such assay systems, there is necessarily an opening in the meter for receiving the test strip. This opening is potentially a means for interfering materials to enter inside the meter and adversely interact with the internal workings of the meter.

As such, there is a need for the development of a device that is capable of providing entry of a test card or strip into a meter but effectively keeps the inside of the meter free of interfering or contaminating agents.

Relevant Literature

References of interest include: U.S. Pat. Nos.: 3,620,676; 3,640,267; 4,088,448; 4,426,451; 4,868,129; 5,104,813; 5,230,866; 5,700,695; 5,736,404; 5,208,163; and European Patent Application EP 0 803 288.

SUMMARY OF THE INVENTION

Test strip holders for use with test strip meters are provided. The subject test strip holders include at least an opening and a lip associated with the opening. The lip element of the subject holders is capable of forming a liquid seal with the upper surface of a test strip upon insertion of the test strip into the opening. In many embodiments, the strip holder is configured to at least partially encompass a sample application region of a test strip upon insertion of the strip into the opening. Also provided are meters on which the subject test holders are present, as well as methods for using the same.

BRIEF DESCRIPTION OF THE FIGURES

FIG. 5 is a graph of data that is used to determine PT time.

DESCRIPTION OF THE SPECIFIC EMBODIMENTS

Figure 1:
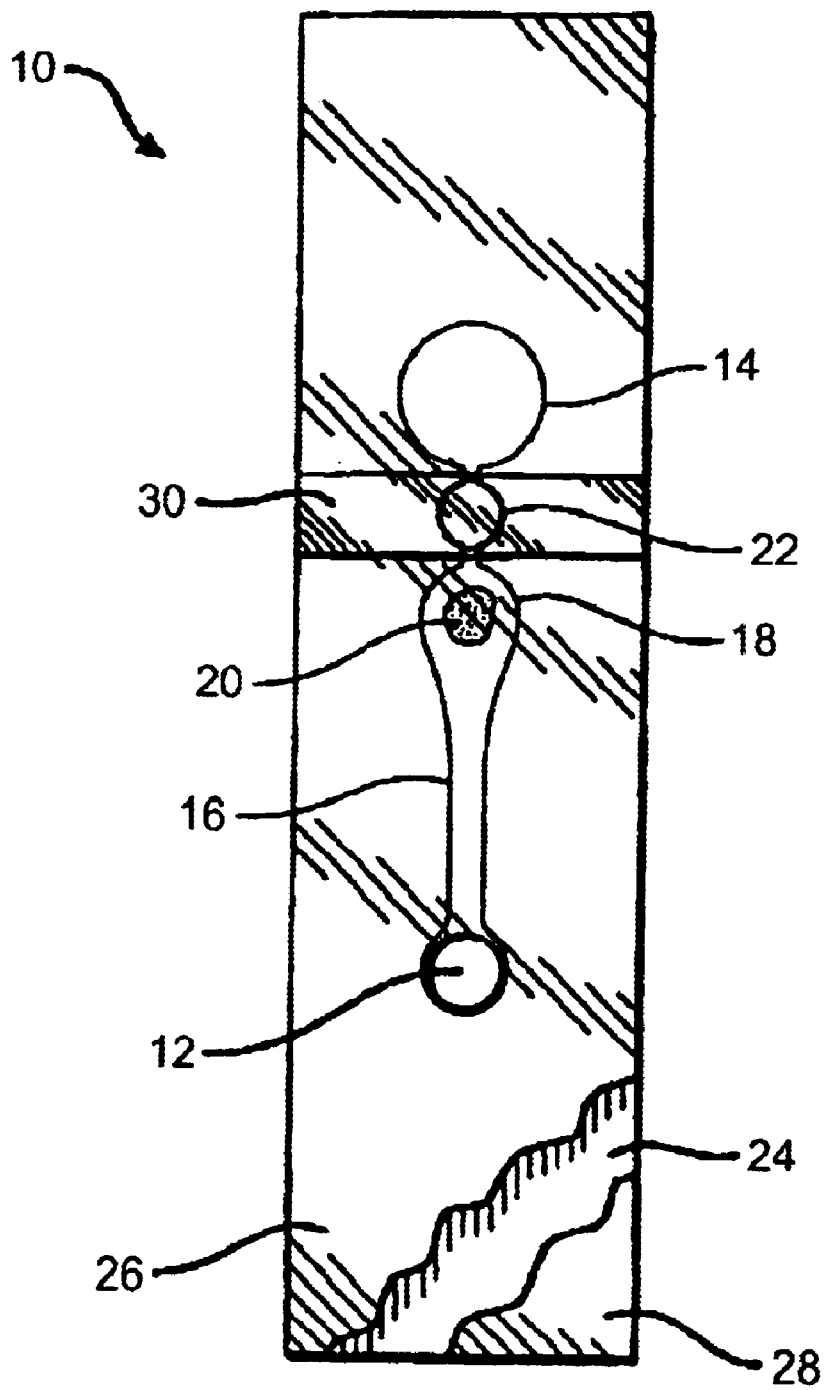
FIG. 1 is a plan view of a bladder including test strip of a system with which the subject strip holders may be employed.

Test strip holders for use with test strip meters are provided. The subject test strip holders include at least an opening and a lip associated with the opening. The lip element of the subject holders is capable of forming a liquid seal with the upper surface of a test strip upon insertion of the test strip into the opening. In many embodiments, the strip holder is configured to at least partially encompass a sample application region of a test strip upon insertion of the strip into the opening. Also provided are meters on which the subject test holders are present, as well as methods for using the same. In further describing the subject invention, the subject test strip holders will be discussed first in greater detail, both generally and in terms of the figures, followed by a review of a representative meter/test strip system in which the subject test strip holders find use, as well as methods for using the same.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Test Strip Holders

As summarized above, the subject test strip holders are configured to be used with meters, where the meters have an opening for receiving at least a portion of test card or strip, e.g. a fluidic test card or device. Representative meters and test strips with which the subject holders find use are disclosed in U.S. patent application Ser. No. 09/333765, filed Jun. 15, 1999; and Ser. No. 09/356248, filed Jul. 16, 1999; the disclosures of which are herein incorporated by reference. In many embodiments, the strip holders of the subject invention are readily removable from the meters with which they are used, i.e. they are not bolted, screwed or otherwise "permanently" affixed to the meter, e.g. they can be snapped onto and off of the meter, etc.

The subject strip holders include an opening for receiving a test strip. The opening is dimensioned so that the test strip is readily movable through the opening, but extra space on either side of the strip is kept to a minimum. While the particular dimensions of the opening may vary depending on the particular meter and fluidic test strip with which the holder is to be used, in many embodiments the opening has a width ranging from about 0.25" to 2", usually from about 0.8" to 1.3" and more usually from about 1.055" to 1.075"; and a height ranging from about 0.015" to 0.125", usually from about 0.02" to 0.06" and more usually from about 0.025" to 0.035".

The subject strip holder is further characterized by having a lip or analogous element that is capable of contacting the surface of a test strip when inserted into the opening and forming a liquid seal. By liquid seal is meant that any space existing between the upper surface of a test strip inserted into the opening and the lip ranges from about 0.000" to 0.002", usually from about 0.0005" to 0.0015", and more usually from about 0.0009" to 0.0011", so that liquid is substantially prevented from entering the internal portion of the meter through the opening of the test strip holder that is placed over the opening of the meter.

To provide for this liquid seal, the subject strip holders further include a raised element or bump that contacts the bottom surface of a test strip when the test strip is inserted into the device. This raised bump or contact is generally configured to contact the test strip beneath the sample application region of the test strip when the test strip is inserted through the strip holder.

In those embodiments where the test strip holder includes the above discussed raised bump or element, the force applied by the above described lip element and the raised bump is substantially the same or identical in location, magnitude and opposite in direction. Depending on the particular embodiment, the force applied by the lip and/or the raised element or bump may range from about 0.01 lb to 0.2 lb, usually from about 0.01 lb to 0.1 lb and more usually from about 0.01 lb to 0.05 lb.

In many embodiments, the strip holder is further characterized by being configured so that a sample application region of a test strip inserted through the opening of the holder is at least partially encompassed, surrounded or encircled by the lip element of the holder. As such, the lip element of the holder may be configured as a partial circle (as shown in the figures), a partial square, triangle etc., which serves to at least partially encompass the sample application region of the test strip when inserted into the opening of the holder.

Figure 6A:
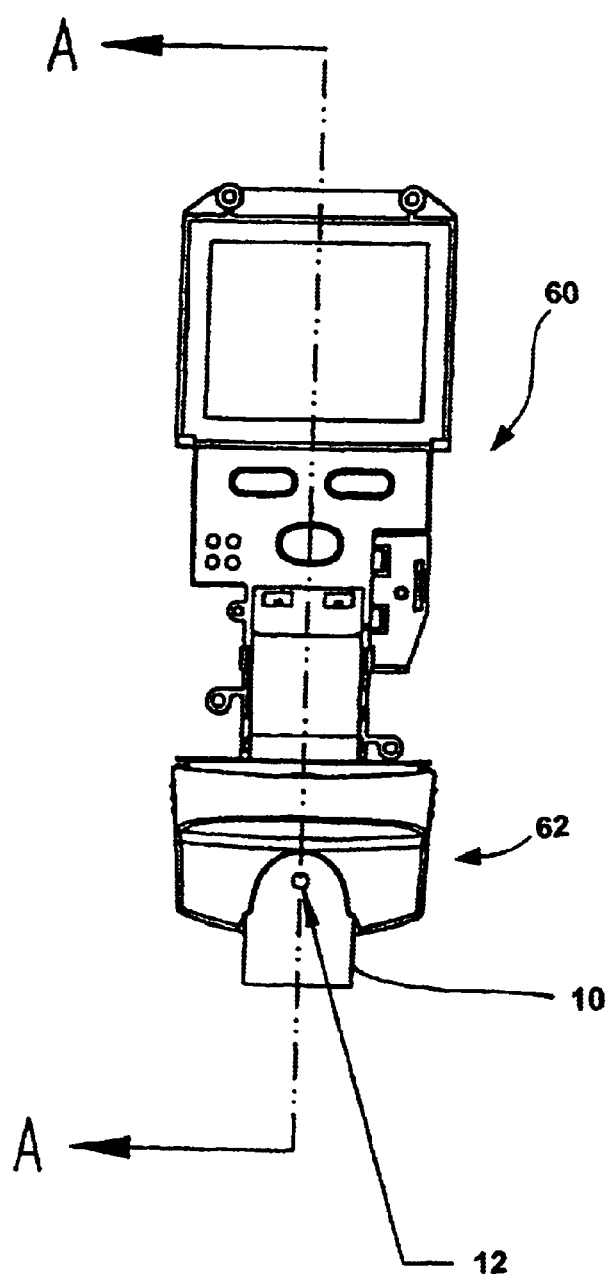
FIG. 6A provides an overhead view of a meter device with a removable strip holder according to the subject invention placed over the opening of the meter.
Figure 6B:
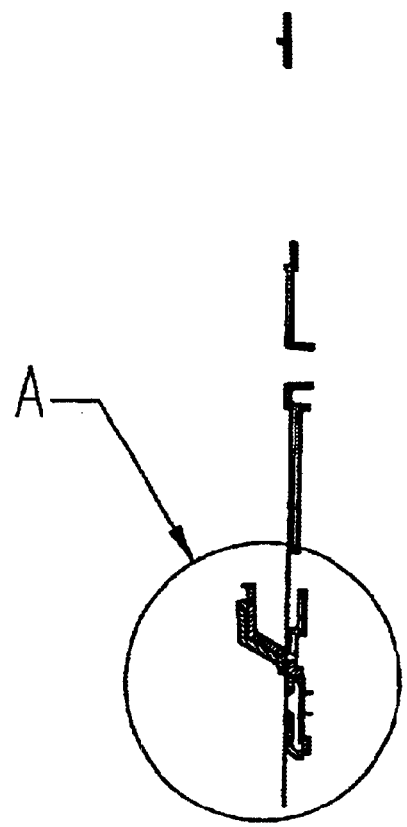
FIG. 6B shows a cross section view of the test strip holder shown in FIG. 6A, where the cross-sectional view is taken along Section A—A as shown in FIG. 6A.
Figure 6C:
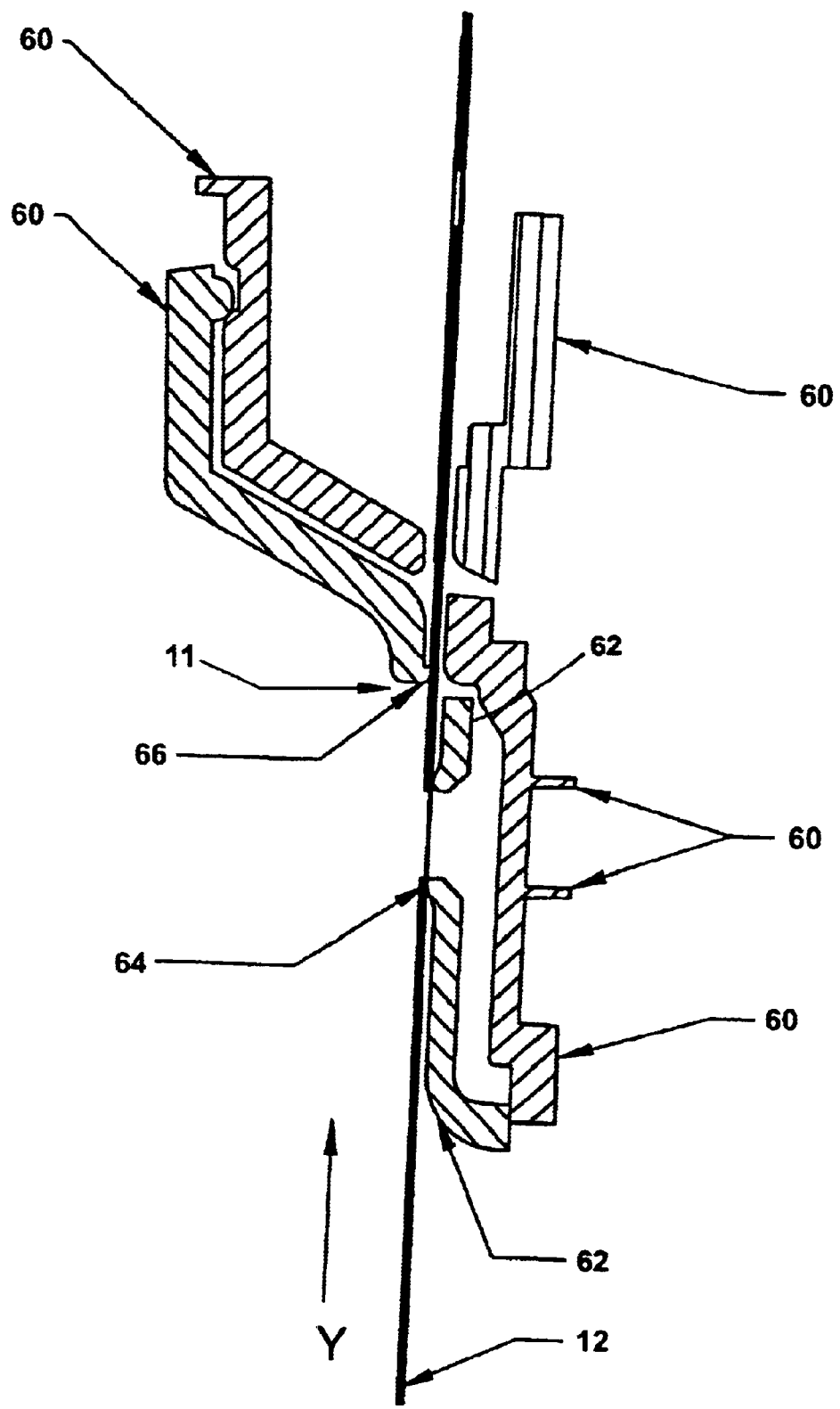
FIG. 6C provides an expanded view of FIG. 6B.

Turning now to the figures, FIG. 6A provides an overhead view of a meter device 60 with a removable strip holder 62 according to the subject invention placed over the opening of the meter. Also shown in FIG. 6A is test strip 10 showing sample application port 12. As is shown in FIG. 6A, the strip holder 62 is configured to at least partially encompass the sample application port 12 by forming a semi-circle around the sample application port 12. FIG. 6B shows a cross sectional view of the test strip holder shown in FIG. 6A, where the cross-sectional view is taken along Section A—A as shown in FIG. 6A. FIG. 6C provides a blow up view of the view shown in FIG. 6B. In FIG. 6C, test strip 12 is inserted into test strip holder 62 and meter 60 in the direction of arrow Y. Lip element 66 of test strip holder 62 presses down on test strip 12 to form a liquid seal at the contact point of the lip element and the upper surface of the strip, while raised element or bump 64 pushes upward on the bottom of the strip with a substantially equal, if not identical force.

The subject test strip holders may be fabricated from any convenient material, where suitable materials include: plastic and metals. The test strip holders may be fabricated using any convenient protocol, where representative protocols include machining, injection molding, compression molding, casting and the like.

Systems

The above described strip holders find use with systems that include fluidic devices or test strips and meters, as described below.

Test Strips

The fluidic test strips of the systems with which the subject strip holders find use are fluidic devices that generally include a sample application area; a bladder, to create a suction force to draw the sample into the device; a measurement area, in which the sample may undergo a change in an optical parameter, such as light scattering; and a stop junction to precisely stop flow after filling the measurement area. Preferably, the devices are substantially transparent over the measurement area, so that the area can be illuminated by a light source on one side and the transmitted light measured on the opposite side.

Figure 2:
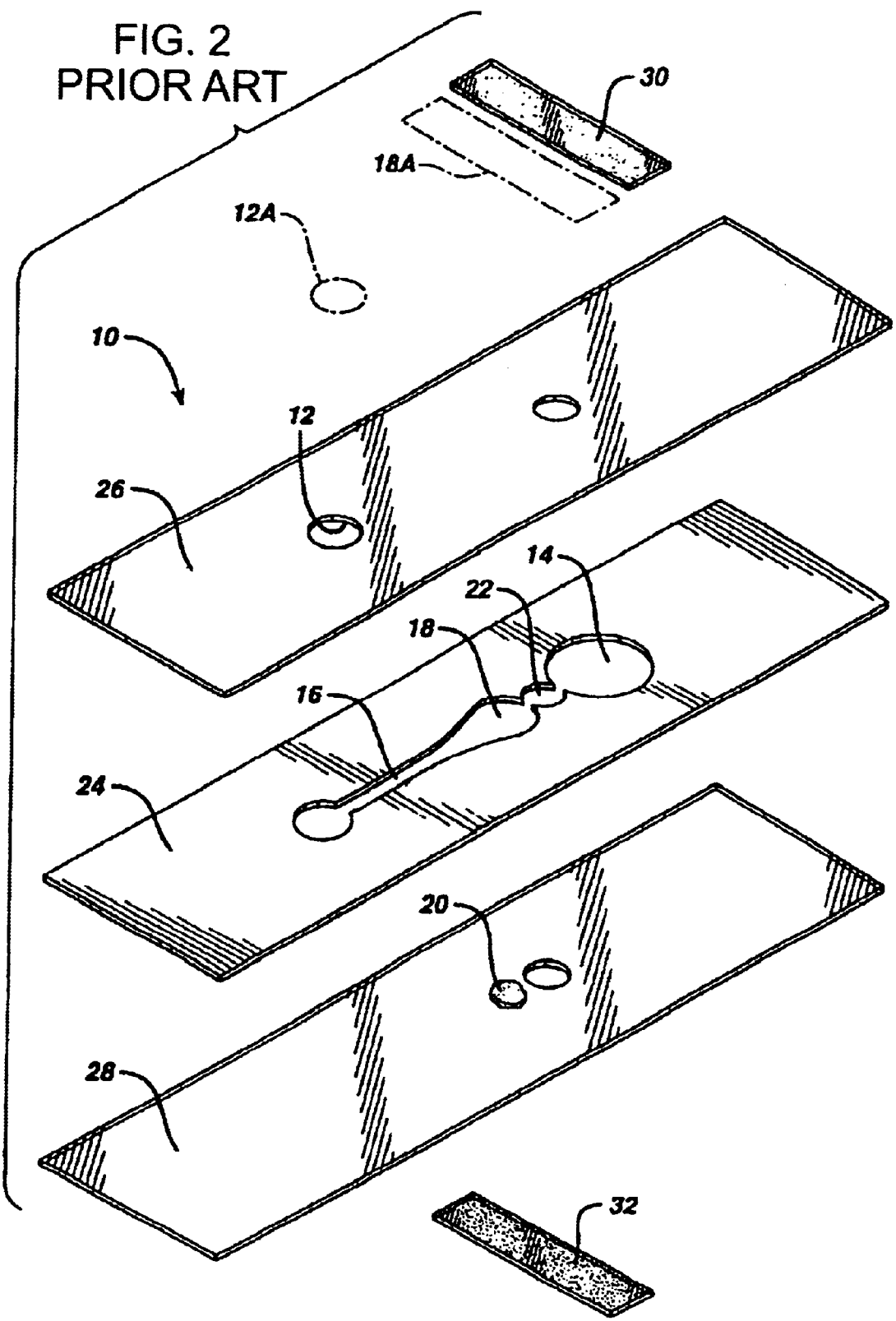
FIG. 2 is an exploded view of the device of FIG. 1.
Figure 3:
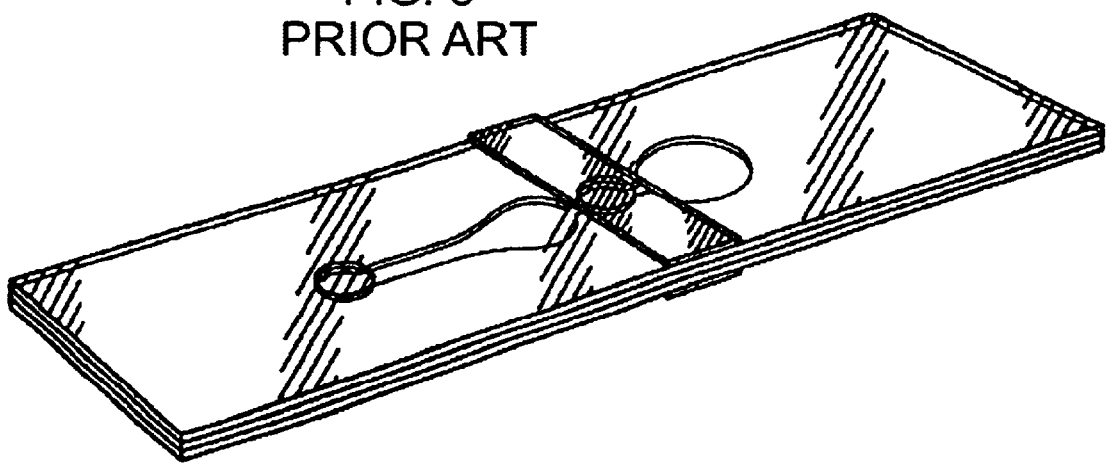
FIG. 3 is a perspective view of the device of FIG. 1.

A representative bladder including test strip with which the subject strip holders find use is shown in FIGS. 1, 2 and 3. FIG. 1 provides a plan view of a test strip 10, while FIG. 2 provides an exploded view and FIG. 3 provides a perspective view of the same representative test strip. Sample is applied to sample port 12 after bladder 14 has been compressed. Clearly, the region of layer 26 and/or layer 28 that adjoins the cutout for bladder 14 must be resilient, to permit bladder 14 to be compressed. Polyester of about 0.1 mm thickness has suitable resilience and springiness. Preferably, top layer 26 has a thickness of about 0.125 mm, bottom layer 28 about 0.100 mm. When the bladder is released, suction draws sample through channel 16 to measurement area 18, which preferably contains a reagent 20. In order to ensure that measurement area 18 can be filled with sample, the volume of bladder 14 is preferably at least about equal to the combined volume of channel 16 and measurement area 18. If measurement area 18 is to be illuminated from below, layer 28 must be transparent where it adjoins measurement area 18.

As shown in FIGS. 1, 2, and 3, stop junction 22 adjoins bladder 14 and measurement area 18; however, a continuation of channel 16 may be on either or both sides of stop junction 22, separating the stop junction from measurement area 18 and/or bladder 14. When the sample reaches stop junction 22, sample flow stops. The principle of operation of stop junctions is described in U.S. Pat. No. 5,230,866; incorporated herein by reference.

As shown in FIG. 2, all the above elements are formed by cutouts in intermediate layer 24, sandwiched between top layer 26 and bottom layer 28. Preferably, layer 24 is double-sided adhesive tape. Stop junction 22 is formed by an additional cutout in layer 26 and/or 28, aligned with the cutout in layer 24 and sealed with sealing layer 30 and/or 32. Preferably, as shown, the stop junction comprises cutouts in both layers 26 and 28, with sealing layers 30 and 32. Each cutout for stop junction 22 is at least as wide as channel 16. Also shown in FIG. 2 is an optional filter 12A to cover sample port 12. The filter may separate out red blood cells from a whole blood sample and/or may contain a reagent to interact with the blood to provide additional information. A suitable filter comprises an anisotropic membrane, preferably a polysulfone membrane of the type available from Spectral Diagnostics, Inc., Toronto, Canada. Optional reflector 18A may be on, or adjacent to, a surface of layer 26 and positioned over measurement area 18. If the reflector is present, the device becomes a transflectance device.

The test strip pictured in FIG. 2 and described above is preferably formed by laminating thermoplastic sheets 26 and 28 to a thermoplastic intermediate layer 24 that has adhesive on both of its surfaces. The cutouts that form the elements shown in FIG. 1 may be formed, for example, by laser- or die-cutting of layers 24, 26, and 28. Alternatively, the device can be formed of molded plastic. Preferably, the surface of sheet 28 is hydrophilic. (Film 9962, available from 3M, St. Paul, Minn.) However, the surfaces do not need to be hydrophilic, because the sample fluid will fill the device without capillary forces. Thus, sheets 26 and 28 may be untreated polyester or other thermoplastic sheet, well known in the art. Similarly, since gravity is not involved in filling, the device can be used in any orientation. Unlike capillary fill devices that have vent holes through which sample could leak, these types of devices vent through the sample port before sample is applied, which means that the part of the strip that is first inserted into the meter is without an opening, reducing the risk of contamination.

Other test strip configurations are also possible, where such alternative device configurations include those that have: a bypass channel; multiple parallel measurement areas; and or multiple in series measurement areas, etc. In addition, the above described laminated structures can be adapted to injection molded structures. A variety of alternative fluidic devices are described in co-pending application Ser. No. 09/333765, filed Jun. 15, 1999; and Ser. No. 09/356248, filed Jul. 16, 1999; the disclosures of which are herein incorporated by reference.

Meters

Figure 4:
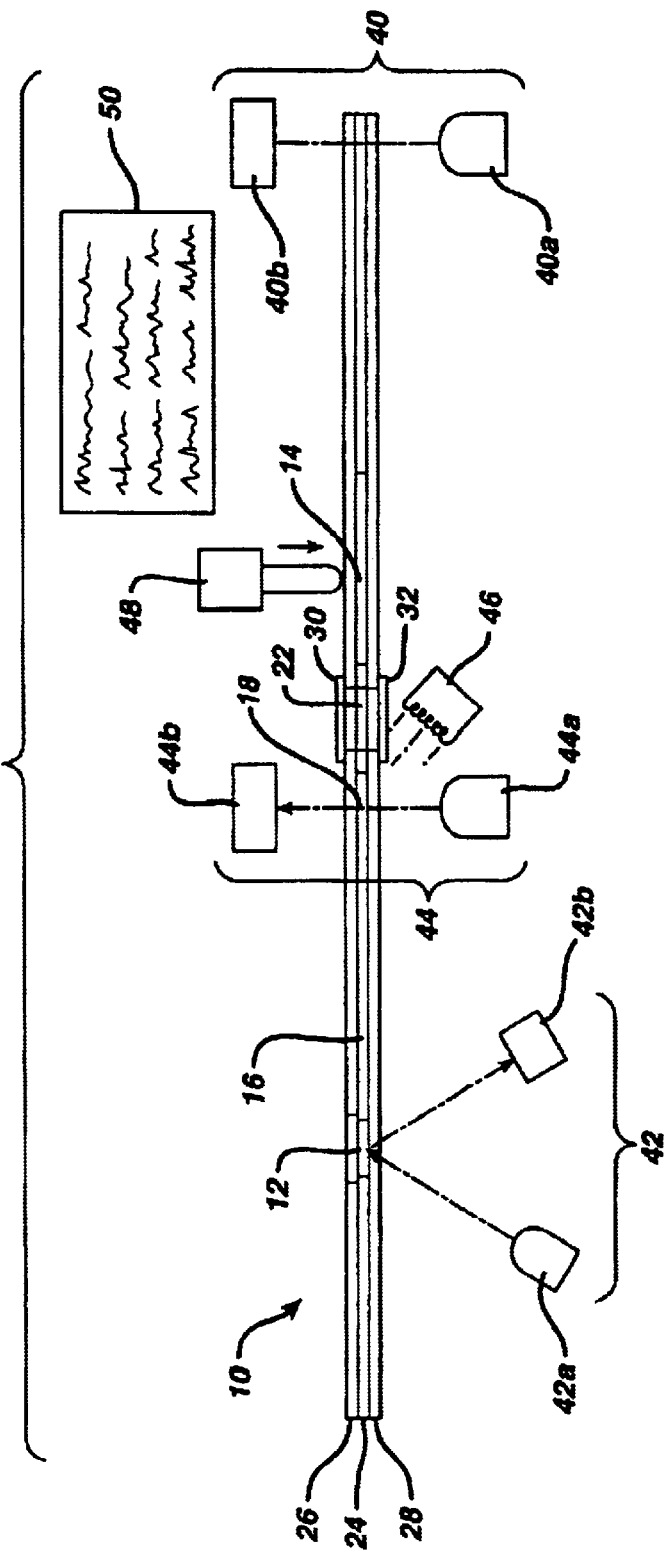
FIG. 4 is a schematic of a meter that includes a strip holder according to the subject invention.

The subject test strip holders find use with meters, generally automated meters, that are designed for use with the above described test strip holders. A representative meter is depicted in FIG. 4, wherein a representative test strip 10 is inserted into the meter. The meter shown in FIG. 4 includes strip detector 40 (made up of LED 40a and detector 40b), sample detector 42 (made up of light source 42a and detector 42b), measurement system 44 (made up of LED 44a and detector 44b), and optional heater 46. The device further includes a bladder actuator 48. The bladder actuator is, in many embodiments, actuated by the strip detector 40 and the sample detector 42, such that when a strip is inserted into the meter and detected by the strip detector, the bladder actuator is depressed, and when the sample is added to the fluidic device or strip inserted into the meter, the bladder actuator is withdrawn so as to decompress the bladder and concomitantly pull sample into the measurement area of the device via the resultant negative pressure conditions. Also present is a meter display 50 that provides for an interface with the user. Finally, the meter is shown with test strip holder 62 positioned over the opening of the meter and strip 10 is inserted into the opening of the test strip holder 62.

Methods of Use

The above described fluidic device/meter systems that include the subject test strip holders are suitable for use in a variety of analytical tests of biological fluids, such as determining biochemical or hematological characteristics, or measuring the concentration in such fluids of analytes such as proteins, hormones, carbohydrates, lipids, drugs, toxins, gases, electrolytes, etc. The procedures for performing these tests have been described in the literature. Among the tests, and where they are described, are the following: (1) Chromogenic Factor XIIa Assay (and other clotting factors as well): Rand, M. D. et al., Blood, 88, 3432 (1996); (2) Factor X Assay: Bick, R. L. Disorders of Thrombosis and Hemostasis: Clinical and Laboratory Practice. Chicago, ASCP Press, 1992.; (3) DRVVT (Dilute Russells Viper Venom Test): Exner, T. et al., Blood Coag. Fibrinol., 1, 259 (1990); (4) Immunonephelometric and Immunoturbidimetric Assays for Proteins: Whicher, J. T., CRC Crit. Rev. Clin Lab Sci. 18:213 (1983); (5) TPA Assay: Mann, K. G., et al., Blood, 76, 755, (1990).; and Hartshorn; J. N. et al., Blood, 78, 833 (1991); (6) APTT (Activated Partial Thromboplastin Time Assay): Proctor, R. R. and Rapaport, S. I. Amer. J. Clin. Path, 36, 212 (1961); Brandt, J. T. and Triplett, D. A. Amer. J. Clin. Path., 76, 530 (1981); and Kelsey, P. R. Thromb. Haemost. 52, 172 (1984); (7) HbAlc Assay (Glycosylated Hemoglobin Assay): Nicol, D. J. et al., Clin. Chem. 29, 1694 (1983); (8) Total Hemoglobin: Schneck et al., Clinical Chem., 32/33, 526 (1986); and U.S. Pat. No. 4,088,448; (9) Factor Xa: Vinazzer, H., Proc. Symp. Dtsch. Ges. Klin. Chem., 203 (1977), ed. By Witt, I; (10) Colorimetric Assay for Nitric Oxide: Schmidt, H. H., et al., Biochemica, 2, 22 (1995).

Turning now to the figures, FIG. 6A provides an overhead view of a meter device 60 with a removable strip holder 62 according to the subject invention placed over the opening of the meter. Also shown in FIG. 6A is test strip 10 showing sample application port 12. As is shown in FIG. 6A, the strip holder 62 is configured to at least partially encompass the sample application port 12 by forming a semi-circle around the sample application port 12. FIG. 6B shows a cross sectional view of the test strip holder shown in FIG. 6A, where the cross-sectional view is taken along Section A—A as shown in FIG. 6A. FIG. 6C provides a blow up view of the view shown in FIG. 6B. In FIG. 6C, test strip 10 is inserted into test strip holder 62 and meter 60 in the direction of arrow Y. Lip element 66 of test strip holder 62 presses down on test strip 10 to form a liquid seal at the contact point of the lip element and the upper surface of the strip, while raised element or bump 64 pushes upward on the bottom of the strip with a substantially equal, if not identical force.

In using the above systems that include the subject test strip holders, the first step the user performs is to turn on the meter, thereby energizing strip detector 40, sample detector 42, measurement system 44, and optional heater 46. The second step is to insert the strip. The strip is inserted through the opening 11 of the test strip holder 62 and into the device. A liquid seal is formed at the contact point between the strip holder and the upper surface of test strip 10. Preferably, the strip is not transparent over at least a part of its area, so that an inserted strip will block the illumination by LED 40a of detector 40b. (More preferably, the intermediate layer is formed of a non-transparent material, so that background light does not enter measurement system 44.) Detector 40b thereby senses that a strip has been inserted and triggers bladder actuator 48 to compress bladder 14. A meter display 50 then directs the user to apply a sample to sample port 12 as the third and last step the user must perform to initiate the measurement sequence. The empty sample port is reflective. When a sample is introduced into the sample port, it absorbs light from LED 42a and thereby reduces the light that is reflected to detector 42b. That reduction in light, in turn, signals bladder actuator 48 to release bladder 14. The resultant suction in channel 16 draws sample through measurement area 18 to stop junction 22. Light from LED 44a passes through measurement area 18, and detector 44b monitors the light transmitted through the sample as it is clotting. Analysis of the transmitted light as a function of time (as described below) permits a calculation of the PT time, which is displayed on the meter display 50. Preferably, sample temperature is maintained at about 37° C. by heater 46.

Figure 4A:
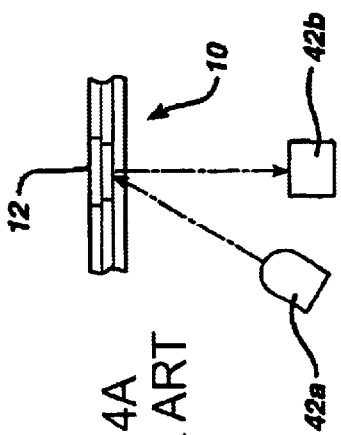
FIG. 4A depicts an alternative embodiment of an element of the meter of FIG. 4.

As described above, the detector senses a sample in sample port 12, simply by detecting a reduction in (specular) reflection of a light signal that is emitted by 42a and detected by 42b. However, that simple system cannot easily distinguish between a whole blood sample and some other liquid (e.g., blood serum) placed in the sample port in error or, even, an object (e.g., a finger) that can approach sample port 12 and cause the system to erroneously conclude that a proper sample has been applied. To avoid this type of error, another embodiment measures diffuse reflection from the sample port. This embodiment appears in FIG. 4A, which shows detector 42b positioned normal to the plane of strip 10. With the arrangement shown in FIG. 4A, if a whole blood sample has been applied to sample port 12, the signal detected by 42b increases abruptly, because of scattering in the blood sample, then decreases, because of rouleaux formation. The detector system 42 is thus programmed to require that type of signal before causing gimbaled bladder actuator 48 to release bladder 14. The delay of several seconds in releasing bladder 14 does not substantially affect the readings described below FIG. 5 depicts a typical "clot signature" curve in which the current from detector 44b is plotted as a function of time. Blood is first detected in the measurement area by 44b at time 1. In the time interval A, between points 1 and 2, the blood fills the measurement area. The reduction in current during that time interval is due to light scattered by red cells and is thus an approximate measure of the hematocrit. At point 2, sample has filled the measurement area and is at rest, its movement having been stopped by the stop junction. The red cells begin to stack up like coins (rouleaux formation). The rouleaux effect allows increasing light transmission through the sample (and less scattering) in the time interval between points 2 and 3. At point 3, clot formation ends rouleaux formation and transmission through the sample reaches a maximum. The PT time can be calculated from the interval B between points 1 and 3 or between 2 and 3. Thereafter, blood changes state from liquid to a semi-solid gel, with a corresponding reduction in light transmission. The reduction in current C between the maximum 3 and endpoint 4 correlates with fibrinogen in the sample.

It is evident from the above results and discussion that the subject test strip holders provide for a simple and convenient way to keep contaminating fluids and other agents out the internal compartments of a meter device during use. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A strip holder for use with a meter, said strip holder comprising:
    a support for receiving a test strip;
    a lip associated with said support, said lip and said support defining an opening therebetween, wherein said lip forms a liquid seal with the upper surface of said test strip and is configured to at least partially encompass a sample application region of said test strip when said test strip is inserted into said opening; and
    a raised bump on said support that contacts the bottom surface of said test strip when inserted into said opening, wherein the force applied by said lip on said top surface of said test strip inserted into said opening is substantially equal and opposite in direction as the force applied by said raised bump on said bottom surface of said test strip inserted into said opening.

2. The strip holder according to claim 1, wherein said lip forms a semi-circle around said sample application region of said test strip.

3. The strip holder according to claim 1, wherein said applied forces range in magnitude from about 0.01 lb to 0.05 lb.

4. A test strip meter system comprising:
    a test strip meter having a measurement system and an entrance for receiving a test strip;
    a test strip holder, wherein said test strip holder comprises:
        a support for receiving a test strip;
        a lip associated with said support, said lip and said support defining an opening therebetween, wherein said lip forms a liquid seal with the upper surface of said test strip and is configured to at least partially encompass a sample application region of said test strip when said test strip is inserted into said opening; and
        a raised bump on said support that contacts the bottom surface of said test strip when inserted into said opening, wherein the force applied by said lip on said top surface of said test strip inserted into said opening is substantially equal and opposite in direction as the force applied by said raised bump on said bottom surface of said test strip inserted into said opening.

5. The system according to claim 4, wherein said strip holder is readily removable from said meter.

6. The system according to claim 4, wherein said system further comprises said test strip inserted into said opening of said strip holder.

7. A method of using a test strip meter system said method comprising:
    providing a test strip meter having a measurement system and an entrance for receiving a test strip;
    (a) providing, wherein said test strip holder comprises:
        (i) a support for receiving a test strip;
        (ii) a lip associated with said opening, wherein said lip forms a liquid seal with the upper surface of said test strip and is configured to at least partially encompass a sample application region of said test strip when said test strip is inserted into said opening; and
        (iii) a raised bump on said support that contacts the bottom surface of said test strip when inserted into said opening, wherein the force applied by said lip on said top surface of said test strip inserted into said opening is substantially equal and opposite in direction as the force applied by said raised bump on said bottom surface of said test strip inserted into said opening; and
    (b) inserting said test strip into said opening and into said meter.

* * * * *